United States Patent
Shalaby et al.

(10) Patent No.: US 9,034,361 B2
(45) Date of Patent: May 19, 2015

(54) HYDROSWELLABLE, SEGMENTED, ALIPHATIC POLYURETHANES AND POLYURETHANE UREAS

(71) Applicant: Poly-Med, Inc., Anderson, SC (US)

(72) Inventors: Shalaby W. Shalaby, Anderson, SC (US); Joel T. Corbett, Anderson, SC (US); Michael Aaron Vaughn, Clemson, SC (US); David R. Ingram, Central, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 14/058,640

(22) Filed: Oct. 21, 2013

(65) Prior Publication Data

US 2014/0046019 A1 Feb. 13, 2014

Related U.S. Application Data

(63) Continuation of application No. 13/415,415, filed on Mar. 8, 2012, now abandoned, which is a continuation of application No. 12/380,391, filed on Feb. 26, 2008, now abandoned.

(60) Provisional application No. 61/069,046, filed on Mar. 12, 2008.

(51) Int. Cl.
| | |
|---|---|
| *A61F 2/30* | (2006.01) |
| *C08G 18/00* | (2006.01) |
| *C08G 64/02* | (2006.01) |
| *A61L 24/00* | (2006.01) |
| *A61L 27/18* | (2006.01) |
| *A61L 27/52* | (2006.01) |
| *C08G 18/12* | (2006.01) |
| *C08G 18/42* | (2006.01) |
| *C08G 18/44* | (2006.01) |
| *C08G 18/48* | (2006.01) |
| *C08G 18/73* | (2006.01) |

(52) U.S. Cl.
CPC ......... *C08G 64/0241* (2013.01); *A61L 24/0021* (2013.01); *A61L 27/18* (2013.01); *A61L 27/52* (2013.01); *A61L 2430/06* (2013.01); *C08G 18/12* (2013.01); *C08G 18/4244* (2013.01); *C08G 18/428* (2013.01); *C08G 18/4283* (2013.01); *C08G 18/44* (2013.01); *C08G 18/4887* (2013.01); *C08G 18/73* (2013.01); *C08G 2230/00* (2013.01)

(58) Field of Classification Search
None
See application file for complete search history.

(56) References Cited

U.S. PATENT DOCUMENTS

2006/0205910 A1* 9/2006 Asplund et al. ............... 528/44
2006/0286143 A1* 12/2006 Shalaby et al. ............... 424/423

* cited by examiner

*Primary Examiner* — H. Sarah Park
(74) *Attorney, Agent, or Firm* — McNair Law Firm, P.A.; Douglas L. Lineberry

(57) ABSTRACT

Hydroswellable, absorbable and non-absorbable, aliphatic, segmented polyurethanes and polyurethane-urea capable of swelling in the biological environment with associated increase in volume of at least 3 percent have more than one type of segments, including those derived from polyethylene glycol and the molecular chains are structurally tailored to allow the use of corresponding formulations and medical devices as carriers for bioactive agents, rheological modifiers of cyanoacrylate-based tissue adhesives, as protective devices for repairing defective or diseased components of articulating joints and their cartilage, and scaffolds for cartilage tissue engineering.

4 Claims, No Drawings

HYDROSWELLABLE, SEGMENTED, ALIPHATIC POLYURETHANES AND POLYURETHANE UREAS

CROSS REFERENCE TO RELATED APPLICATION

This application is a Continuation of U.S. Ser. No. 13/415,415, filed Mar. 8, 2012 which claims the benefit of prior provisional application, U.S. Ser. No. 61/069,046, filed Mar. 12, 2008, and is a continuation of U.S. Ser. No. 12/380,391, filed Feb. 26, 2009, all of which are hereby incorporated by reference in their entirety.

FIELD OF THE INVENTION

The present invention is directed to hydroswellable (or water-swellable) absorbable and non-absorbable aliphatic, segmented polyurethanes and polyurethane-ureas, which can undergo swelling when placed in the biological environment manifested through an at least 3 percent increase in volume by virtue of having a highly hydrophilic polyalkylene oxide as an inherent part of their segmented chain molecules. By varying the type and fraction of the different segments constituting the copolymers, their pharmaceutical and biomedical applications as non-absorbable and absorbable materials entail their use in carriers for the controlled release of bioactive agents, rheological modifiers of absorbable and non-absorbable cyanoacrylate tissue adhesives, synthetic cartilage-like materials, and scaffolds for tissue engineering cartilage tissues.

BACKGROUND OF THE INVENTION

Polyurethanes represent a main class of synthetic elastomers applied for long-term, medical implants as they present tunable chemical properties, excellent mechanical properties, good blood compatibility, and also can be designed to degrade in biological environments [A. Rechichi et al., J. Biomed. Mater. Res., 84-A, 847 (2008)]. More specifically, polyether-urethane (PEU) and polyether-urethane-urea (PEUU) elastomers have long been considered ideal for use in many implanted devices, in spite of occasionally cited drawbacks [M. A. Schubert et al., J. Biomed. Mater. Res., 35, 319 (1997); B. Ward et al., J. Biomed. Mater. Res., 77-A, 380 (2008)]. Of the cited drawbacks are those associated with (1) the generation of aromatic diamines, which are considered to be toxic upon degradation of segmented copolymers made using aromatic diisocyanates for interlinking; (2) chain degradation due to oxidation or radiation degradation of the polyether component of segmented copolymers, and particularly those which encounter frequent mechanical stresses in the biological environment; and (3) chemical degradation in chemically and mechanically hostile biological environments of the urethane links of segmented copolymers and particularly those comprising reactive aromatic urethane linkages.

Liquid solventless, complex polymeric compositions, which thermoset at ambient temperatures through additional polymerization of a two-component system, wherein the first component comprises amine or acrylate-terminated polyurethanes or polyurethane-ureas and the second component comprises di- or polyacrylates have been described in U.S. Pat. No. 4,742,147. However, the prior art is virtually silent on self-standing PEU and PEUU liquid solventless compositions for use in pharmaceutical formulations and/or medical devices. Similarly, the prior art on polyether-urethanes is practically silent on hydroswellable (or water-swellable) systems, in spite of the fact that it covered elastomeric, segmented, hydrophilic polyether-urethane-based, lubricious coating compositions based on aromatic diisocyanate and polyethylene glycol (U.S. Pat. No. 4,990,357)—it did not suggest a self-standing material for medical device applications.

Collective analysis of the prior art on PEU and PEUU as discussed above regarding the drawbacks of the disclosed systems, absence of self-standing liquid and hydroswellable copolymers, and recognition of the need for new materials exhibiting properties that cannot be met by those of the prior art, provided a strong incentive to explore the synthesis and evaluation of the PEU and PEUU systems subject of this invention, which are structurally tailored for their effective use in existing and new applications.

SUMMARY OF THE INVENTION

The present invention is directed to different types of hydroswellable (or water-swellable) polyurethanes and polyurethane-ureas.

A specific aspect of the invention describes a hydroswellable, segmented, aliphatic polyurethane comprising polyoxyalkylene chains, covalently linked to polyalkylene carbonate chains, which are interlinked with aliphatic urethane segments, the composition exhibiting an at least 3 percent increase in volume when placed in the biological environment, wherein the polyoxyalkylene glycol chains comprise at least one type of oxyalkylene sequences selected from the group represented by oxyethylene, oxypropylene, oxytrimethylene, and oxytetramethylene repeat units and the alkylene carbonate chains are trimethylene carbonate sequences, and wherein the urethane segments are derived from at least one diisocyanate selected from the group represented by tetramethylene diisocyanate, hexamethylene diisocyanate, octamethylene diisocyanate, decamethylene diisocyanate, dodecamethylene diisocyanate, lysine-derived diisocyanate, and cyclohexane bis-(methylene isocyanate). Meanwhile, the polyurethane is made by reacting a liquid polyoxylene alkylene glycol comprising oxyethylene or a combination of oxyethylene and oxypropylene sequences that are end-grafted with trimethylene carbonate wherein the resulting product is interlinked with 1,6-hexane diisocyanate, and wherein the liquid polyalkylene glycol is a polyethylene glycol having, preferably, a molecular weight of about 400-500 Da. From a pharmaceutical application perspective, the polyurethanes can be used as vehicles for a controlled release formulation of at least one bioactive agent selected from the group of agents known to exhibit anti-inflammatory, anesthetic, cell growth promoting, antimicrobial, antiviral, and antineoplastic activities. In a specific pharmaceutical application, the controlled release formulation comprises at least one antimicrobial agent after treating periodontitis or bone infection selected from the group represented by doxycycline, gentamicin, vancomycin, tobramycin, clindamycin, and mitomycin and the periodontal formulation may include absorbable microparticles made of acid-terminated glycolide-based polyester and a liquid excipient such as a liquid polyethylene glycol and an alkylated or acylated derivative thereof. In a second group of pharmaceutical applications, the controlled release formulation comprises a liquid polyethylene glycol or an alkylated or acylated derivative thereof as an excipient and at least one bioactive agent selected from the group represented by paclitaxel, carboplatin, miconazole, leflunamide, ciprofloxacin, and a recombinant protein for treating breast or ovarian cancer in humans or animals. Additionally, for tissue repair applications, the polyurethane can be admixed with one or more cyanoacrylate monomer for use as a rheological modifier of tissue adhesives, wherein the one or more cyanoacrylate monomer is part of an absorbable or non-absorbable tissue adhesive formulation comprising stabilizers against premature polymerization, free radically and anionically, and at least one monomer selected from the group represented by ethyl-, butyl-, isobutyl-, methoxypropyl-, methoxyethyl-, and methoxybutyl cyanoacrylate.

Another specific aspect of the present invention deals with a hydroswellable, segmented, aliphatic polyurethane-urea comprising polyoxyalkylene chains covalently interlinked with polyalkylene urethane segments, which are further interlinked with aliphatic urea chain segments, the composition exhibiting at least 5 percent increase in volume when placed in the biological environment, wherein the polyalkylene glycol chains comprise at least one type of oxyalkylene sequences selected from the group represented by oxyethylene, oxypropylene, oxytrimethylene, and oxytetramethylene repeat units and the urethane segments are derived from at least one diisocyanate selected from the group represented by hexamethylene diisocyanate, hexamethylene diisocyanate, octamethylene diisocyanate, decamethylene diisocyanate, dodecamethylene diisocyanate, 1,4 cyclohexane diisocyanate, lysine-derived diisocyanate, and cyclohexane bis(methylene isocyanate) and wherein the resulting polyoxyalkylene urethane molecules having at least one isocyanate terminal group are chain-extended with an alkylene diamine selected from the group represented by ethylene-, trimethylene, tetramethylene-, hexamethylene-, and octamethylene-diamine, thus forming polyetherurethane-urea segmented chains.

A clinically important aspect of the invention deals with a hydroswellable, segmented, aliphatic polyurethane-urea comprising polyoxyalkylene chains covalently interlinked with polyalkylene urethane segments, which are further interlinked with aliphatic urea chain segments, the composition exhibiting at least 5 percent increase in volume when placed in the biological environment, wherein the polyurethane-urea (1) can be chemically crosslinked, wherein the crosslinking is achieved using an alkylene diisocyanate; (2) can exhibit microporosity with a practically continuous cellular structure; (3) can comprise at least one covalently bonded aromatic group to stabilize the chain against radiation and oxidation degradation; and/or (4) can be used as an artificial cartilage for restoring the function of diseased or defective articulating joints in humans and animals.

An important aspect of this invention deals with a hydroswellable, segmented, aliphatic polyurethane comprising polyoxyalkylene chains covalently linked to polyester or polyester-carbonate chain segments, interlinked with aliphatic urethane segments, the composition exhibiting at least 5 percent increase in volume when placed in the biological environment, wherein the polyester or polyester-carbonate chain segments are derived from at least one cyclic monomer selected from the group represented by ϵ-caprolactone, trimethylene carbonate, p-dioxanone, 1,5-dioxepan-2-one, l-lactide, dl-lactide, glycolide, and a morpholinedione. Meanwhile, the polyurethane can exhibit microporosity with practically continuous cellular structure for use as an absorbable scaffold or part thereof for cartilage tissue engineering, with or without the aid of a cell growth promoting agent therein.

For prolonged effective device performance, the present invention is directed to a hydroswellable, segmented, aliphatic polyurethane-urea comprising a combination of linear functionalized polysiloxane and polyoxyalkylene chains interlinked with polyalkylene urethane segments, which are further interlinked with aliphatic urea chain segments, the composition exhibiting at least 5 percent increase in volume when placed in the biological environment, wherein the polyoxyalkylene chain comprises at least one type of oxyalkylene sequences selected from the group represented by oxyethylene, oxypropylene, oxytrimethylene, and oxytetramethylene repeat units and the functionalized polysiloxane is derived from bis-hydroxyalkyl-terminated polysiloxane comprising at least dimethoxysiloxane internal sequences and two hydroxyalkyl or aminoalkyl terminals and further wherein the urethane segments are derived from at least one diisocyanate selected from the group represented by hexamethylene diisocyanate, octamethylene diisocyanate, decamethylene diisocyanate, dodecamethylene diisocyanate, 1,4 cyclohexane diisocyanate, lysine-derived diisocyanate, and cyclohexane bis(methylene isocyanate) and wherein the resulting polyoxyalkylene urethane molecules having at least one isocyanate terminal group are further chain-extended with an alkylene diamine selected from the group represented by ethylene-, trimethylene, tetramethylene-, hexamethylene- and octamethylene-diamine, thus forming polyetherurethane-urea segmented chains, wherein the polyurethane-urea (1) can be chemically crosslinked wherein the crosslinking is achieved using an alkylene diisocyanate; (2) can exhibit microporosity with a practically continuous cellular structure; (3) can comprise at least one covalently bonded aromatic group to stabilize the chain against radiation and oxidation degradation; and/or (4) can be used as an artificial cartilage for restoring the function of diseased or defective articulating joints in humans and animals.

DETAILED DESCRIPTION OF PREFERRED EMBODIMENTS

The present invention is generally directed to the tailored synthesis of the following families of hydroswellable polymers. The term "hydroswellable" is intended to indicate that the polymers swell and increase in volume in the presence of water.

(1) Relatively slow-absorbing, segmented polyether-carbonate-urethanes (PECU) as vehicles for the controlled release of bioactive agents including those known to exhibit or unexpectedly exhibit antimicrobial, microbicidal, antineoplastic, and antiviral activities wherein the typical PECUs (a) exhibit <20 percent or no solubility in water; (b) are made to be liquids at about 50° C.; (c) have a weight average molecular weight exceeding 10 kDa; (d) swell in an aqueous environment leading to an increase of volume of at least 3 percent; and (e) are miscible in water-soluble, low viscosity liquid excipients, such as polyethylene glycol 400, to facilitate their use as injectable formulations that undergo gel-formation when introduced to aqueous biological sites—the ratio of the PECU to the excipient can be modulated in concert with the active agent solubility, its intended release site, and preferred release rate.

(2) The PECUs of Item 1 as rheology modifiers of cyanoacrylate-based tissue adhesive formulations wherein (a) the PECU is used to increase the viscosity of the uncured tissue adhesive; (b) render the cured tissue adhesive more compliant and able to conform with the biological site—this is achieved by decreasing the cured adhesive modulus due to the presence of the low modulus PECU at concentrations of at least one weight percent; (c) the cyanoacrylate tissue adhesive comprises at least one monomer selected from the group represented by ethyl-, n-butyl-, isobutyl-, methoxypropyl-, ethoxypropyl-, methoxybutyl-, and octyl-cyanoacrylate; and (d) the cyanoacrylate tissue adhesive contains at least one stabilizer to prevent premature polymerization by an anionic and free radical mechanism—typical examples of these are pyrophosphoric acid and butylated hydroxyl anisole for stabilization against anionic and free radical polymerization, respectively.

(3) Relatively fast-absorbing, segmented aliphatic polyether-ester urethanes (PEEU) and polyether-carbonate-ester urethanes (PECEU) as vehicles for the controlled release of bioactive agents including those known to exhibit or unexpectedly exhibit antimicrobial, microbicidal, antiviral, and antineoplastic activities wherein the typical PEEUs and PECEUs (a) exhibit limited (<20 percent) or no solubility in water; (b) are made to be liquids at about 50° C.; (c) have a weight average molecular weight exceeding 10 kDa; (d) swell in an aqueous environment leading to an increase of volume of at least 3 percent; and (e) are miscible in water-soluble, low viscosity liquid excipients, such as polyethylene glycol 400 and an alkylated or acylated derivative thereof, to facilitate their use as injectable formulations that undergo gel-formation when introduced to aqueous biological sites—the ratio of the PECU to the excipient can be modulated in concert with the active agent solubility, its intended release site, and preferred release rate.

(4) The PEEUs and PECEUs of Item 3 as rheology modifiers of absorbable cyanoacrylate-based tissue adhesive formulations wherein (a) the PEEU or PECEU is used to increase the viscosity of the uncured tissue adhesive; (b) render the cured tissue adhesive more compliant and able to conform with the biological site—this is achieved by decreasing the cured adhesive modulus due to the presence of the low modulus PEEU or PECEU at concentrations of at least one weight percent; (c) the cyanoacrylate tissue adhesive comprises an alkoxyalkyl cyanoacrylate, such as methoxypropyl cyanoacrylate or a mixture of an alkoxyalkyl cyanoacrylate and an alkyl cyanoacrylate, such as ethyl cyanoacrylate; and (d) the cyanoacrylate tissue adhesive contains at least one stabilizer to prevent premature polymerization by an anionic and free radical mechanism—typical examples of these are pyrophosphoric acid and butylated hydroxy anisole for stabilization against anionic and free radical polymerization, respectively.

(5) Essentially biostable, non-absorbable, segmented, aliphatic polyether urethane-ureas (PEUU) as flexible, solid, linear or chemically crosslinked polymers for use primarily as cartilage-like materials, which undergo swelling and deswelling upon cyclic application of compressive force for prolonged periods, while practically maintaining their initial properties, wherein the typical PEUUs (a) exhibit limited (<5 percent) or no solubility in water; (b) can be fabricated into films, sheets or caps for articulating bones in humans or animals with essentially no display of first order thermal transitions and exhibiting ultimate elongation exceeding 200 percent, reversible elongation of >10 percent and an at least 5 percent increase in volume when immersed in water for less than two hours; (c) have a molecular weight corresponding to an inherent viscosity of more than unity using hexafluoroisopropyl alcohol (HFIP) as a solvent when present as linear molecular chains; and (d) can be fabricated into different desirable forms or geometries by solution casting.

(6) Highly biostable, non-absorbable, segmented, aliphatic PEUU as in Item 5 comprising a polysiloxane (e.g., poly dimethyl siloxane segment) to improve its oxidation stability in the biological environment.

(7) Highly biostable, non-absorbable, segmented, aliphatic PEUU as in Item 5 comprising a covalently bonded chemical entity capable of minimizing or eliminating radiation during radiation sterilization, and oxidative degradation when placed in the biological environment. These radiation and oxidation stabilizers can be in the form of polymerizable (as in diols) derivatives of hydroxyl aromatic compounds or low molecular polymers comprising oxy-aromatic groups and hydroxyl end-groups. Such simple or polymeric diols can be mixed with the polyether diol prior to end-grafting with other monomers and interlinking with diisocyanate.

(8) Absorbable, segmented, aliphatic polyether-ester urethane (APEEU) and polyether-ester-carbonate urethane (APEECU) as scaffolds for cartilage tissue engineering wherein the typical APEEUs and APEECUs (a) comprise polyoxyalkylene chains (such as those derived from polyethylene glycol and block or random copolymers of ethylene oxide and propylene oxide) covalently linked to polyester or polyester-carbonate segments (derived from at least one monomer selected from the group represented by trimethylene carbonate, ε-caprolactone, lactide, glycolide, p-dioxanone, 1,5-dioxepan-2-one, and a morpholinedione) and interlinked with aliphatic urethane segments derived from 1,6 hexamethylene-, 1-4 cyclohexane-, cyclohexane-bis-methylene-, 1,8 octamethylene- or lysine-derived diisocyanate; (b) display at least 5 percent increase in volume due to swelling, when placed in the biological environment; (c) have a microporous structure with average pore size ranging between about 20 and 400 micron and practically continuous cell structure; and (d) are suitable for use as an absorbable scaffold for cartilage tissue engineering wherein the scaffold may contain at least one bioactive agent which may include at least one cell growth promoter.

From a clinical perspective, compositions and formulations or devices thereof subject of the present invention can be used in a broad-range of applications including (1) injectable gel-forming liquid formulations for the controlled delivery of bioactive agents for treating periodontitis, nail infection, bone infection, a variety of bacterial and fungal infections, and different forms of cancers; (2) in situ-forming, extrudable luminal liner for the controlled drug delivery at the luminal wall of vaginal canals and blood vessels; (3) a rheology modifier for essentially non-absorbable and absorbable cyanoacrylate-based tissue adhesive formulations; (4) cartilage-like covers to protect defective or diseased articulating joints; and (5) an absorbable scaffold for cartilage and soft tissue engineering.

Further illustrations of the present invention are provided by the following examples:

EXAMPLE 1

Synthesis and Characterization of a Typical Polyether-carbonate-urethane, P-1

For an initial charge, poly(ethylene glycol) ($M_n$=400 Da) (0.15 moles) and tin(II) 2-ethyl hexanoate ($3.53 \times 10^{-4}$ moles) were added to a 500 mL, 3-neck, round-bottom flask equipped with a PTFE coated magnetic stir bar. The contents were heated to 70° C. and allowed to stir for 10 minutes. For a second charge, trimethylene carbonate (0.882 moles) was added and the contents were heated to 135° C. Conditions were maintained until practically complete monomer conversion was achieved. The magnetic stir bar was removed and replaced by a stainless steel mechanical stirrer. The polymer was cooled to room temperature. For a third charge, 1,6-diisocyanatohexane (0.12 moles) was added and the contents were stirred until complete mixing was achieved. The contents were stirred and heated to 100° C. Conditions were maintained for 1.25 hours. The polymer was allowed to cool to room temperature and then dissolved in an equal part of tetrahydrofuran. The polymer solution was treated with 5 mL of 2-propanol at 55° C. then precipitated in cold water. The purified polymer was isolated and dried to a constant weight at 55° C. on a rotary evaporator. The purified polymer was characterized for molecular weight by GPC using tetrahydrofuran as the mobile phase which resulted in an $M_n$, $M_w$, $M_p$, and PDI of 11 kDa, 19 kDa, 18 kDa, and 1.7 respectively. Identity and composition were confirmed by FT-IR and NMR, respectively.

EXAMPLE 2

Synthesis and Characterization of Liquid Polyether-Ester-Urethane

General Method

For an initial charge, poly(ethylene glycol) ($M_n$=400 Da) and tin(II) 2-ethyl hexanoate were added to a 500 mL, 3-neck, round-bottom flask equipped with a PTFE coated magnetic stir bar. The contents were heated to 70° C. and allowed to stir for 10 minutes. For a second charge, dl-lactide and glycolide were added and the contents were heated to 135° C. Conditions were maintained until practically complete monomer conversion was achieved. The magnetic stir bar was removed and replaced with a stainless steel mechanical stirrer. The polymer was cooled to room temperature. For a third charge, 1,6-diisocyanatohexane was added and the contents were stirred until complete mixing was achieved. The contents were stirred and heated to 100° C. Conditions were maintained for 1.25 hours. The polymer was allowed to cool to room temperature and then dissolved in an equal part of tetrahydrofuran. The polymer solution was treated with 5 mL of 2-propanol at 55° C. then precipitated in cold water. The purified polymer was dried to a constant weight at 55° C. on a rotary evaporator. The purified polymer was characterized for molecular weight by GPC using tetrahydrofuran as the mobile phase. Identity and composition were confirmed by FT-IR and NMR, respectively.

EXAMPLE 3

Synthesis and Characterization of Typical Polyether-ester-urethanes Using the General Method of Example 2, P-2, P-3, and P-4

Polyether-ester-urethanes P-2, P-3, and P-4 were prepared using the method of Example 2 with 0.15, 2.225, 0.15 moles of polyethylene glycol ($M_n$=400 Da), $2.60 \times 10^{-4}$, $3.18 \times 10^{-4}$, $2.60 \times 10^{-4}$ moles of tin(II) 2-ethyl hexanoate, 0.52, 0.64, 0.52 moles of dl-lactide, 0.13, 0.16, 0.13 moles of glycolide, and 0.18, 0.18, 0.12 moles of 1,6-diisocyanatohexane, respectively, Polymers P-2, P-3, and P-4 were characterized for molecular weight by GPC using tetrahydrofuran as the mobile phase which resulted in $M_n$ of 11, 9, and 9 kDa, $M_w$ of 20, 14, and 15 kDa, Mp of 20, 12, 14, kDa, and PDI of 1.9, 1.6, and 1.6, respectively. Identity and composition were confirmed by FT-IR and NMR, respectively.

EXAMPLE 4

Synthesis and Characterization of Typical Polyether-ester-urethanes Using the General Method of Example 2, P-5 to P-8

Polyether-ester-urethanes P-5, P-6, P-7 and P-8 were prepared using the method of Example 2 with 0.15, 0.22, 0.22, 0.22 moles of polyethylene glycol ($M_n$=400 Da), $3.53 \times 10^{-4}$, $4.17 \times 10^{-4}$, $4.22 \times 10^{-4}$, $4.12 \times 10^{-4}$ moles of tin(II) 2-ethyl hexanoate, 0.88, 0.94, 1.08, and 0.80 moles of trimethylene carbonate (TMC), 0.00, 0.31, 0.19, and 0.43 moles of glycolide, and 0.12, 0.18, 0.18, and 0.18 moles of 1,6-diisocyanatohexane, respectively. Polymers P-5, P-6, P-7 and P-8 were characterized for molecular weight by GPC using tetrahydrofuran as the mobile phase which resulted in $M_n$ of 11, 10, 10, and 9 kDa, $M_w$ of 19, 14, 16, and 14 kDa, Mp of 18, 13, 15, and 14 kDa, and PDI of 1.7, 1.4, 1.6 and 1.5, respectively. Identity and composition were confirmed by FT-IR and NMR, respectively.

EXAMPLE 5

Synthesis and Characterization of Acetylated Polyethylene Glycol-400 (PG-4A) for Use as a Diluent Liquid Excipient of P-2 to P-8

Predried polyethylene glycol having a molecular weight of about 400 Da (25.6 g) was mixed in a round-bottom flask (equipped for magnetic stirring and refluxing) under dry nitrogen atmosphere with purified acetic anhydride (22.2 g). The mixture was stirred for 1 hour at 40° C. and then at 100° C. for 3 hours. At the conclusion of the reaction, the contents of the flask were heated under reduced pressure to remove the acetic acid reaction by-product and excess acetic anhydride. The acetylated product (PG-4A) was characterized for identity by infrared spectroscopy and molecular weight by gel permeation chromatography (GPC).

EXAMPLE 6

Synthesis, Characterization, and Testing of a Typical Film-Forming Polyether-urethane-urea, PEUU-I Poly(ethylene glycol)-block-poly(propylene glycol)-block-poly(ethylene glycol) ($M_n$=14,600 Da, 82.5 wt % poly(ethylene glycol) ($1.64 \times 10^{-3}$ moles) and poly(tetramethylene glycol) ($M_n$=2,900 Da) ($1.93 \times 10^{-2}$ moles) were added to a 500 mL glass resin kettle equipped for mechanical stirring and vacuum. The contents were dried at 140° C. under reduced pressure for 3 hours and then cooled to room temperature. N,N-Dimethylacetamide (190 mL) was added and the contents were heated to 60° C. and stirred until a homogeneous solution was obtained. The contents were cooled to room temperature and 1,6-diisocyanatohexane ($3.14 \times 10^{-2}$ moles) was added. The contents were stirred until a homogeneous solution was obtained. Tin(II) 2-ethyl hexanoate ($3.53 \times 10^{-4}$ moles) in the form of a 0.2M solution in 1,4-dioxane was added. The contents were stirred until a homogeneous solution was obtained and then heated to 100° C. under stirring conditions. Conditions were maintained for 2 hours. The contents were cooled to room temperature. Ethylene diamine ($1.05 \times 10^{-2}$ moles) was added in the form of a 1.16M solution in N,N-dimethylacetamide under stirring conditions. Upon gelation, the stirrer was stopped and conditions were maintained for 24 hours. The polymer was purified by subsequent extractions with water and acetone then dried to a constant weight at 45° C. under reduce pressure. The purified polymer was characterized for molecular weight by inherent viscosity in hexafluoroisopropanol which resulted in an inherent viscosity of 5.71 dL/g. Identity was confirmed by FT-IR.

EXAMPLE 7

Preparation and Properties of n-Butyl Cyanoacrylate-based Tissue Adhesive Formulation Using P-5 from Example 4 as a Rheology Modifier This entailed mixing and characterizing the different monomer combinations and using a selected mixture to prepare a typical adhesive formulation A pure methoxypropyl cyanoacrylate (MPC) and pure n-butyl cyanoacrylate (BC) monomers and combination thereof were characterized for their rheological properties, measured in terms of their comparative viscosity as listed Table I. Ratios of 90/10, 50/50, 20/80, and 10/90 (by weight) of MPC to butyl cyanoacrylate were mixed. Monomers were weighed in a centrifuge tube and placed on a shaker for 15 minutes. The rheological data of the resulting compositions are summarized in described in Table I.

TABLE 1

Cyanoacrylate Monomer Compositions and Their Rheological Data[a]

| Monomer Ratios | Monomer Composition | Comparative Viscosity (s) |
|---|---|---|
| 100 | BC | 3.30 ± 0.06 |
| 10:90 | MPC:BC | 3.42 ± 0.06 |
| 20:80 | MPC:BC | 3.55 ± 0.10 |
| 50:50 | MPC:BC | 4.23 ± 0.14 |
| 90:10 | MPC:BC | 5.16 ± 0.17 |
| 100 | MPC | 6.15 ± 0.36 |

[a]Measured in terms of time (in seconds) to collect 0.3 mL of liquid adhesive, transferring vertically by gravity through an 18-guage, 1.5 in. long syringe needle.

A selected formulation was prepared by dissolving 3% (by weight) of P1 in a 20/80 (by weight) mixture of methoxypropyl cyanoacrylate and butyl cyanoacrylate containing 500 ppm of butylated hydroxyanisole and 3.3 ppm of pyrophosphoric acid stabilizers against free radical and anionic polymerization, respectively. More specifically, this entailed the following steps: (1) the P1 polymer was added to a flask and dried at 80° C. for 3 hours; (2) the cyanoacrylate monomers and the stabilizers were added; and (3) the resulting mixture was stirred at 80° C. until it became homogenous. The resulting formulation exhibited a comparative adhesive viscosity of 12.63 s and an adhesive joint strength of 28.35 N (using a fabric peel test).

EXAMPLE 8

Preparation and Properties of Absorbable Cyanoacrylate Tissue Adhesive Formulation Using P-6 of Example 4 as a Rheology Modifier The adhesive formulation was prepared by dissolving 5% (by weight) of P-6 in a 90/10 (by weight) mixture of methoxypropyl cyanoacrylate and ethyl cyanoacrylate containing 500 ppm of butylated hydroxyanisole and 3.3 ppm of pyrophosphoric acid as stabilizers against free radical and anionic polymerization, respectively. More specifically, this entailed the following steps: (1) the P3 polymer was added to a flask and dried at 80° C. for 3 hours; (2) the cyanoacrylate monomers and stabilizers were added; and (3) the resulting mixture was stirred at 80° C. until it became homogenous. The resulting formulation exhibited a comparative adhesive viscosity of 6.74 s and an adhesive joint strength of 34.96 N (using a fabric peel test).

EXAMPLE 9

Preparation of a Doxycycline Hyclate Controlled Release Formulation Using P-2 from Example 3 and Determination of the Drug Release Profile This entailed a three-step process, namely, mixing P-2 (from Example 3) with a diluent liquid excipient (from Example 5), acetylated polyethylene glycol-400 (PG-4A), preparation of an active formulation, and monitoring the drug release profile.

Mixing P-2 with PG-4A—For this, P-2 (3.2691 g) was placed in a glass vial and PG-4A (1.7603 g) was added. The contents of the vial were heated to 50° C. and mechanically mixed until a homogenous mixture developed. The final mixture was 65 weight percent P-2 with the remainder consisting of PG-4A.

Preparation of Active Formulation—To prepare a liquid vehicle, an aliquot of 2.0237 g of the P-2/PG-4A mixture was transferred to a glass vial, and doxycycline hyclate (434 mg) was added to the vial. Microparticles of acid-terminated polyglycolide (433 mg) were added to the contents of the vials. This was followed by heating to 50° C. and mixing mechanically to obtain a homogenous mixture. The resulting mixture was 70 weight percent liquid vehicle, 15 percent polyglycolide microparticles, and 15 percent doxycycline hyclate.

Release Study—The active formulation (1.0230 g) was placed in a small glass vial and heated to 50° C. to flow into bottom of vial and create a uniform coating and then was allowed to cool to room temperature. Phosphate buffer (10 mL, pH 7.2) was placed into the glass vial, which was transferred to a 37° C. incubator. The buffered solution (with released drug) was withdrawn at predetermined time points and replaced with 10 mL of fresh buffer. Aliquots of the release buffer were assayed by reverse phase HPLC, using a Waters Chromatography System with a C18 column, a gradient of 15-30% acetonitrile over 10 minutes, and detection at 350 nm; the amount of doxycycline released over time was determined. The HPCL data indicated a cumulative release at 23, 94, and 163 hours of 16%, 31%, and 45%, respectively.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:
1. An artificial cartilage for use in articulating joints of mammals comprising:
   a biostable aliphatic polyurethane comprising an alternating block copolymer wherein the biostable aliphatic polyurethane further comprises prepolymer segments and interlinking segments wherein the prepolymer segments further comprise terminal urethane groups that are interlinked via aliphatic urea groups;
   the biostable aliphatic polyurethane further comprising polyoxyalkylene chains covalently interlinked with polyalkylene urethane segments;
   wherein the artificial cartilage is flexible, hydroswellable and has a reversible elongation of greater than 10 percent;
   wherein the polyoxyalkylene chains comprise at least one oxyalkylene sequence selected from the group consisting of oxyethylene, oxypropylene, oxytrimethylene, or oxytetramethylene repeat units;
   wherein the artificial cartilage is interlinked using an alkylene diisocyanate selected from the group consisting of hexamethylene diisocyanate, octamethylene diisocyanate, decamethylene diisocyanate, dodecamethylene diisocyanate, 1,4 cyclohexane diisocyanate, lysine-derived diisocyanate, or cyclohexane bis(methylene isocyanate);

wherein the artificial cartilage further comprises at least one covalently bonded group to reduce radiation and oxidation degradation;

wherein the artificial cartilage exhibits ultimate elongation of greater than 200 percent and reversible elongation of greater than 10 percent;

wherein the biostable aliphatic polyurethane comprises a prepolymer and a chain extender and the biostable aliphatic polyurethane has a molar ratio of prepolymer to chain extender of substantially 1:1; and wherein the artificial cartilage exhibits an at least 5 percent increase in volume when immersed in water for less than two hours.

2. The artificial cartilage of claim 1, wherein the artificial cartilage is chain-extended via an alkylene diamine selected from the group consisting of ethylene-trimethylene diamine, tetramethylene, hexamethylene diamine, or octamethylene diamine.

3. The artificial cartilage of claim 1, wherein the at least one covalently bonded group is selected from the group consisting of polysiloxane, hydroxyl aromatic compounds, or low molecular weight polymers, wherein the low molecular weight polymers comprise oxy-aromatic groups and hydroxyl end-groups.

4. The artificial cartilage of claim 1, wherein the artificial cartilage is formed into a film, a sheet, or a cap for articulating bones.

* * * * *